United States Patent
Spechtmeyer

(10) Patent No.: US 10,362,979 B2
(45) Date of Patent: Jul. 30, 2019

(54) APPARATUS FOR RECOGNIZING AND LOCATING EMOTIONS AND THOUGHTS BY MEASURING THE INFRARED PULSE RADIATION

(71) Applicant: Horst-Wolfgang Spechtmeyer, Brühl (DE)

(72) Inventor: Horst-Wolfgang Spechtmeyer, Brühl (DE)

( * ) Notice: Subject to any disclaimer, the term of this patent is extended or adjusted under 35 U.S.C. 154(b) by 107 days.

(21) Appl. No.: 15/319,067

(22) PCT Filed: Nov. 4, 2015

(86) PCT No.: PCT/DE2015/000530
§ 371 (c)(1),
(2) Date: Dec. 15, 2016

(87) PCT Pub. No.: WO2016/074657
PCT Pub. Date: May 19, 2016

(65) Prior Publication Data
US 2017/0150914 A1    Jun. 1, 2017

(30) Foreign Application Priority Data

Nov. 13, 2014  (DE) .......................... 10 2014 016 834

(51) Int. Cl.
*A61B 5/16*    (2006.01)
*A61B 5/00*    (2006.01)
(Continued)

(52) U.S. Cl.
CPC ............ *A61B 5/165* (2013.01); *A61B 5/0064* (2013.01); *A61B 5/0075* (2013.01);
(Continued)

(58) Field of Classification Search
CPC ....... A61B 5/165; A61B 5/0077; A61B 5/725; A61B 5/0075; A61B 5/742; A61B 5/7225;
(Continued)

*Primary Examiner* — Rex R Holmes

(57) ABSTRACT

FIG. 1 shows the components of the measuring apparatus for recognizing and locating emotions and thoughts by measuring the infrared pulse radiation in the sequence of the measured value pre-processing: localization tube 1, infrared detector 2, amplifier 3, analog/digital conversion 4, analysis program 5 and display 6, wherein the components of the measuring apparatus have the following features: the localization tube 1 receives the infrared pulses, which are produced by changes in the body heat of a creature and emitted by a small surface, and partially reflects said infrared pulses several times at the inner wall and focuses said pulses on the infrared detector 2; the infrared detector 2 which is designed to be able to receive only AC voltage signals and not DC voltage signals converts the infrared beams into electrical signals; the amplifier 3 amplifies these signals; the signals are digitized during the analog/digital conversion 4; the analysis program 5 creates time signals, amount spectra and differential spectra for the total measuring time or for time sections in different mental dispositions of the creature being investigated and creates a characteristic mental spectrum in the pulse frequency range of approximately 0.01 to 10 Hz; the results for the different mental dispositions of the creature being investigated can be seen on the display 6 and can be compared, with the result that different emotions such as joy or sorrow can be recognized, for example. In addition to the measuring apparatus, it is possible to use a transmitter which flashes on a small body surface and whose light pulses contain infrared portions. This has the advantage of amplifying pulse frequencies which have already occurred and of allowing the pulse frequencies which have not yet appeared during mental activity to emerge.

10 Claims, 3 Drawing Sheets

Figure 1:
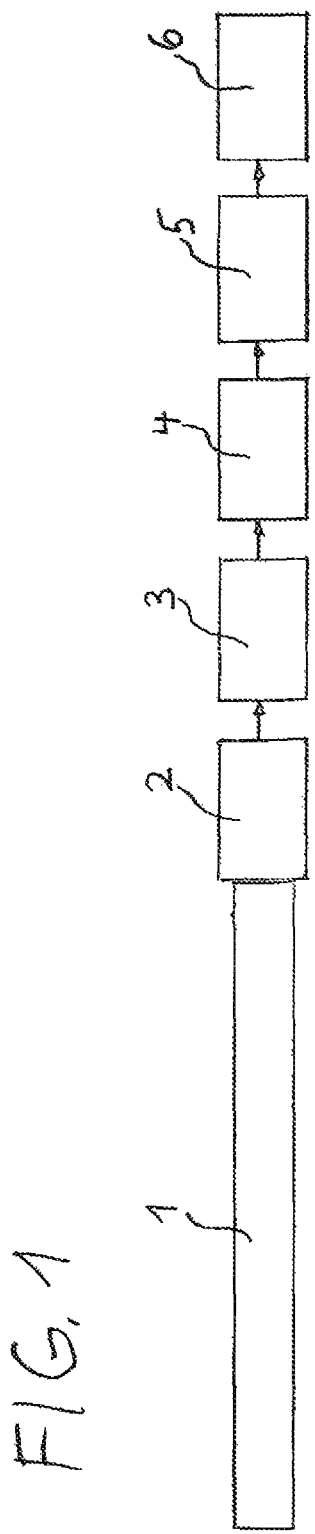

(51) Int. Cl.
*A61B 5/01* (2006.01)
*A61B 5/026* (2006.01)

(52) U.S. Cl.
CPC ............ *A61B 5/0077* (2013.01); *A61B 5/015* (2013.01); *A61B 5/725* (2013.01); *A61B 5/7225* (2013.01); *A61B 5/7278* (2013.01); *A61B 5/742* (2013.01); *A61B 5/0261* (2013.01); *A61B 2562/0233* (2013.01); *A61B 2562/0271* (2013.01); *A61B 2576/00* (2013.01)

(58) Field of Classification Search
CPC ..... A61B 5/7278; A61B 5/015; A61B 5/0064; A61B 2562/0233; A61B 2576/00; A61B 2562/0271; A61B 5/0261
See application file for complete search history.

APPARATUS FOR RECOGNIZING AND LOCATING EMOTIONS AND THOUGHTS BY MEASURING THE INFRARED PULSE RADIATION

It is known that with a measurement apparatus according to patent No. 10 2006 014 143 with measurement times >20 s in the frequency range between 0.1 and 1 Hz you can detect a characteristic spectrum of feelings. Here for identification of emotions pulse frequencies of feelings are pulled apart by using a parabolic mirror. Emitted from great surfaces, for example from the head, the infrared pulses are measured which the body himself produces by heat changes during a feeling.

The invention disclosed in claim 1 while retaining the principle of measurement and the benefits, for example the determination of the nature and the strength of a feeling, that an investigation of thoughts and feelings is also possible for small body surfaces.

Here, the frequency range is extended from 0.01 to 10 Hz.

The function of the parabolic mirror and the possibility to measure a small area, is fulfilled by the locating tube: it takes the infrared pulses, caused by body heat changes of a living creature and emitted from a small surface, and these partly reflects several times on the inner wall and focuses the pulses on the infrared detector. The pulse frequencies of the thoughts and feelings are pulled apart by the locating tube like the parabolic mirror.

In claim 2 is set so that the window of the infrared detector has a band pass filter of 8-14μ. Concerning the body temperature of warm-blooded animals like a man this is the right wavelength range for measuring the periodic irregularities of the heat emission.

By the measuring device described in the patent claims 1 and 2 the body's infrared emission can be measured on small areas and thoughts and feelings can be associated with pulse frequencies. In claim 3, in addition to the measuring device, a transmitter is used flashing on a small body surface and whose light pulses containing infrared portions. This has the advantage to strengthen already occurring pulse frequencies and to generate pulse frequencies not yet caused by mental activity.

The claims 4 and 5 suggest how such a transmitter might look. The optical part of the transmitter consists of an electric bulb and a similar locating tube as for the measuring device, so that the infrared pulses can irradiate small body surfaces. The transmitter has a flashing device for frequencies in the range from about 0.01 Hz to 10 Hz.

Claims 6 to 9 are apparatus descriptions which relate both to the measuring device as well as to the transmitter. Patent claim 6 serves to increase the intensity of the pulse frequency spectrum. Claim 7 shows how one can couple the infrared detector and the light source, at least partially emitting infrared pulses, to the locating tubes.

Claim 8 minimizes the errors that may occur due to strong movements. Therefore, the measuring device and the transmitter are fixed in a stand and the man for example sits loose having the examined body points near the ends of the locating tubes. In claim 9 the possibility is considered that the locating tubes of the transmitter and/or the measuring device can show in different directions to the body surface so that the influence of the cell arrangement can be found.

Claim 10 opens the new way to use the measuring device and the transmitter at any point of the body to track down intellectual and emotional cells.

In summary one can say that profitably instead of a parabolic mirror a locating tube is inserted, partially reflecting and refracting the infrared pulses, also emitted from the measurement object, on the inner wall, so that the frequency width of the pulse frequency spectrum is enlarged, and focusing the infrared pulses onto the pyroelectric detector, however forming a thin, collimated beam to scan small body surfaces. Thus, one can determine for example what kind of feeling is at any body point.

Additionally an infrared transmitter is used to irradiate small body surfaces. Thus one can determine which pulse frequencies are generated when the infrared transmitter irradiates with a given pulse frequency. It should be noted that pulse frequencies correspond to a specific activity of emotional or intellectual nature.

When positioning the measuring device and the transmitter any body parts of a living creature can be selected. For example, one can compare the pulse frequency spectra of the path from one hand to the other with the path from one foot to the other. Or you compare the pulse frequency spectra, when the measuring device and the transmitter are directed at the same distance to the forehead and the abdomen. Thus, intellectual and emotional cells can be detected.

If the measuring device is not perpendicular to the body surface, one can determine the angle dependence of the pulse frequency spectrum.

The following examples of the invention are listed.

FIG. 1 principally shows the measurement apparatus.

Figure 2:
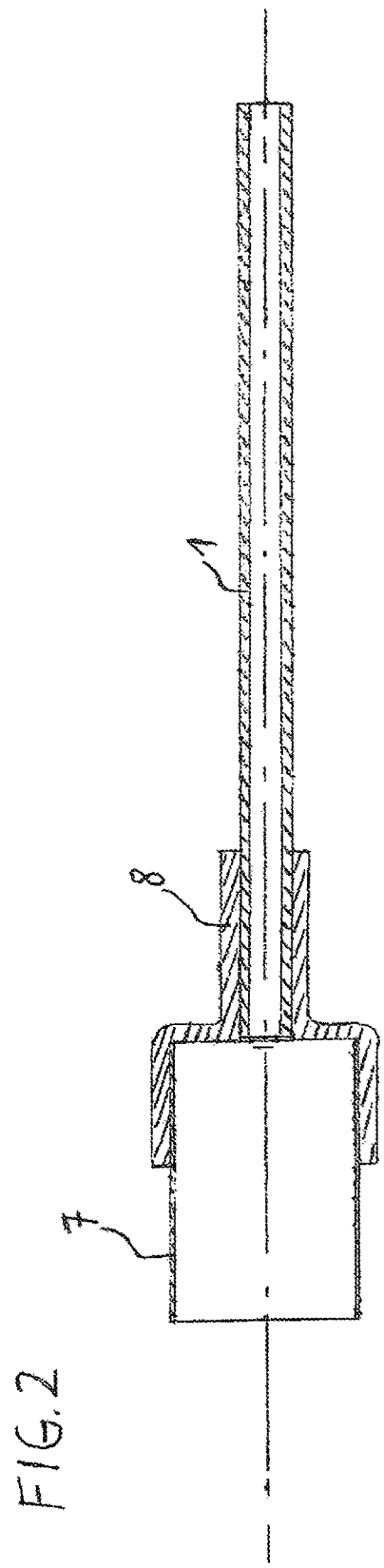
Figure 3:
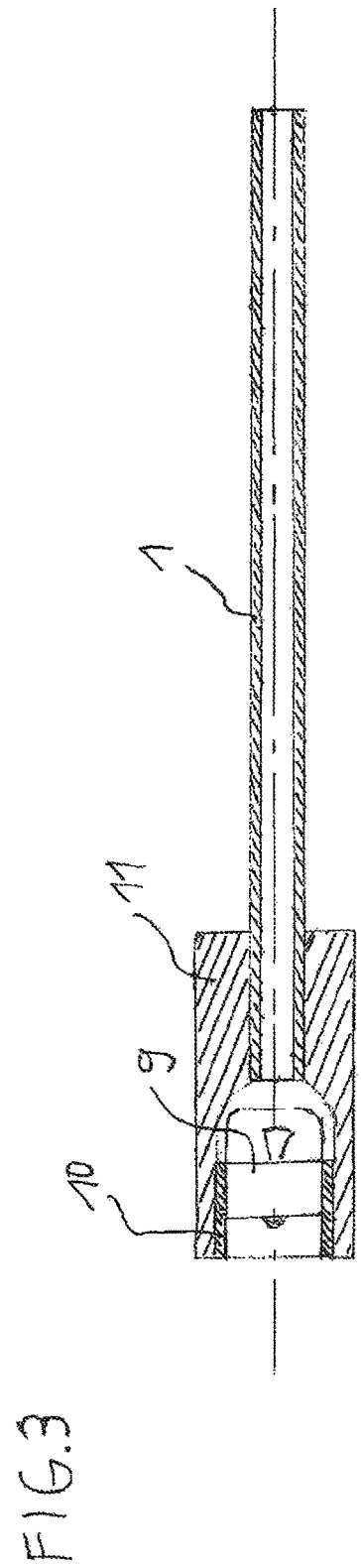

FIGS. 2 and 3 show embodiments of the measuring device respectively the transmitter.

Figure 4:
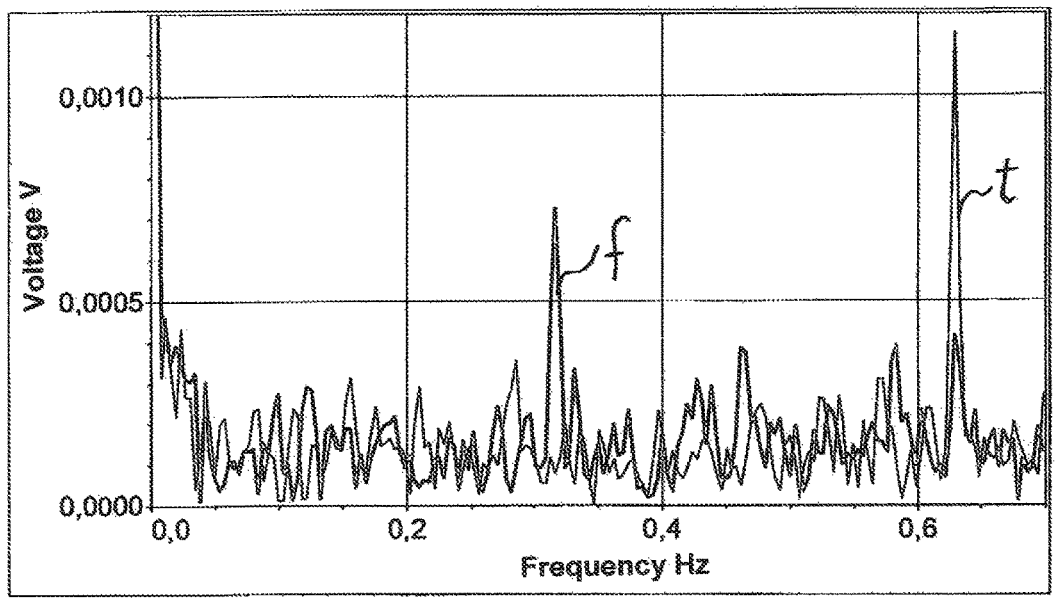
Figure 5:
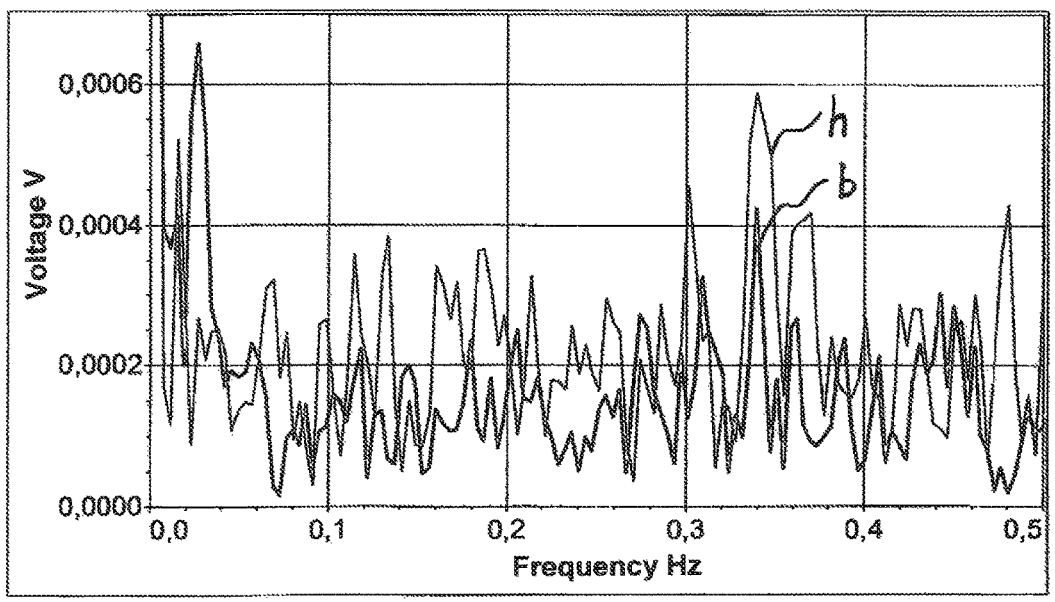

In FIG. 4 the pulse frequency spectrum for the first and in FIG. 5 for the second experiment can be seen.

FIG. 1 shows the components of the measuring apparatus for recognizing and locating emotions and thoughts by measuring the infrared pulse radiation in the sequence of the measured value pre-processing: localization tube 1, infrared detector 2, amplifier 3, analogue/digital conversion 4, analysis program 5 and display 6, wherein the components of the measuring apparatus have the following features: the localization tube 1 receives the infrared pulses, which are produced by changes in the body heat of a creature and emitted by a small surface, partially reflects said infrared pulses several times at the inner wall and focuses said pulses on the infrared detector 2; the infrared detector 2 which is designed to be able to receive only AC voltage signals and not DC voltage signals converts the infrared beams into electrical signals; the amplifier 3 amplifies these signals; the signals are digitized during the analogue/digital conversion 4; the analysis program 5 creates time signals, amount spectra and differential spectra for the total measuring time or for time sections in different mental dispositions of the creature being investigated and creates a characteristic mental spectrum in the pulse frequency range of approximately 0.01 to 10 Hz; the results for the different mental states of the creature being investigated can be seen on the display 6 and can be compared, with the result that different emotions such as joy or sorrow can be recognized, for example.

In the first experiment only the measuring apparatus according to FIG. 1 was used by the embodiment of FIG. 2.

The technical data of the infrared detector 2 were: band pass filter: 8 to 14μ; diameter of the active area: 2 mm; detector material: Lithium Tantalate; sensitivity at body temperature 500K and chopper frequency 1 Hz: 900 V/W; supply voltage: 3-15 V; working voltage: 6V.

The infrared detector 2 was mounted together with the amplifier 3 (60 dB at 1 to 1000 Hz) in a metal cylinder 7 (diameter 30 mm; length 90 mm).

The locating tube 1 was a 400 mm long aluminium tube with the outer diameter of 8 mm and the inside diameter of 5 mm. The inner surface of the aluminum tube had not been specially treated to make it brilliant. Metal cylinder 7 and locating tube 1 were closely together and coupled with a fitting 8 made of aluminium.

The amplified signals (1 or 2 channels) were transferred by screened wires, confectioned with latch connectors, to an aluminium terminal. The connection between terminal and laptop was confectioned by a 37-pin-connector and an A/D card 4. The digital transforming 4 was done by a 12-bit-card. The sampling rate of the card was 0.006 Hz up to 100 kHz. The input range was ±10 V.

The software for computer aided measuring and analysing of vibration, noise and earthquake was used. By the digital signal analysis DSA diagrams of time signals and—after eliminating the diagram ends by a block cursor of 300 s—pulse frequency spectra were produced (analysis program 5).

The examined person was sitting on a chair; the locating tube 1 of the measuring device was at a distance of about 5 mm in front of the forehead. The locating tube 1 was perpendicular to the forehead surface. The head was kept quiet without thinking that it was not allowed to tremble.

Aided by imagination also produced by invented stories expressing the special feeling, one concentrated on the feelings "sorrow" respectively "joy" in many trials. In the display 6 you could see and compare the results according to the different feelings of the measurement object.

FIG. 4 shows a pulse frequency spectrum of the first experiment.

In each case, a prominent peak can be seen: at 0.6294 Hz for the feeling "sorrow" (t) and at 0.3166 Hz for the feeling "joy" (f).

In FIG. 3 is a model of the transmitter. As light source a 5 W-12V-electric bulb 9 was used which was pushed to a copper socket 10 having the diameters 15 and 17 mm and the length of 30 mm. The performance of the locating tube 1 was identical with that of the measuring device. Socket 10 and locating tube 1 were coupled by a fitting 11 of polyethylene so that the filament of the electric bulb 9 was not too far from the end of the locating tube.

In the second experiment, the measuring device and the transmitter were used. In this case, both locating tubes were spaced about 5 mm to the body surface and oriented perpendicular to the body surface. The blinker frequency was 0.375 Hz. Thoughts and feelings were avoided. There were 2 cases investigated in order to compare them. First, the locating tubes were fixed at a distance of 8 cm in the same body height on the bare belly. After that, one locating tube was directed on the right and the other locating tube on the left hand palm. Otherwise, the same experimental conditions were made as for the first experiment.

FIG. 5 shows the pulse frequency spectrum for the second experiment. The peaks of the path that runs from the palms of the hands (h) via the arms and the upper body are higher than that of the belly-path (b). However, there are many peaks with the same or approximately the same pulse frequencies, where the same waveform is slightly shifted. If we count that the belly-way is only 8 cm and hand-path is about 160 cm, so the number of emotion viable cells in the abdominal area seems to be greater than in the arms and shoulders.

The invention claimed is:

1. A measuring device for recognizing and locating of feelings and thoughts by measuring an infrared pulse radiation comprising:
   a locating tube;
   an infrared detector;
   an amplifier;
   an analogous/digital conversion;
   an analysis program;
   a display;
   the locating tube receiving infrared pulses, caused by body heat changes of a living creature and radiated from a small body surface, and partly reflected several times on an inner wall and focused on the infrared detector;
   the infrared detector which is designed so that it only can receive AC signals and no DC voltage signals, converts infrared radiation into electrical signals;
   the amplifier amplifying the signals;
   at the analogous/digital conversion the signals being digitized;
   the analysis program creating time signals, amount spectra and difference spectra for an entire measurement time or time sections in various mental dispositions of the living creature and creating a characteristic spectrum in a mental pulse frequency range of about 0.01 to 10 Hz; and
   on the display results being capable of being seen in different mental states of the living creature and being compared so that various emotions including joy and sadness are visible and so that thoughts are visible.

2. The measuring device according to claim 1, wherein a window of the infrared detector has a band-pass filter of 8 to 14μ.

3. The measuring device according to claim 1, wherein a transmitter is used which flashes on the small body surface and whose light pulses contain infrared portions.

4. The measuring device according to claim 3, wherein an optical part of the transmitter consists of an electric bulb and another locating tube.

5. The measuring device according to claim 3, wherein the transmitter has a flashing device for frequencies in the range from about 0.01 Hz to 10 Hz.

6. The measuring device according to claim 1, wherein another locating tube of the transmitter has another inner wall, the inner wall and the other inner wall are highly reflective for infrared radiation and dimensions of the inner wall and the other inner wall are approximate to dimensions of the window of the infrared detector respectively a light source of the transmitter and one end of the locating tubes is positioned as close as possible to the window of the infrared detector respectively the light source.

7. The measuring device according to claim 1 further comprising a metal cylinder, wherein the metal cylinder, lodging the infrared detector and the amplifier, respectively a pipe socket of the light source of the transmitter are coupled to the locating tubes by fittings made of metal or insulating material.

8. The measuring device according to claim 1, wherein the fittings of the measuring device and the transmitter are fixed in a stand and the small body surface receiving respectively emitting infrared pulses is as close as possible to an end of the locating tube and an end of the other locating tube of the transmitter.

9. The measuring device according to claim 1, wherein the locating tube and the other locating tube of the transmitter can show in different directions to the small body surface.

10. The measuring device according to claim 1, wherein the infrared pulse radiation generated by the transmitter can strike at any part of the small body surface of the living creature and it's action can be measured by the measuring device at any other part of the body surface of the living creature, or when measuring a forehead the change of pulse frequencies in response to flashing frequencies can be determined, or when comparing a path from one foot to another foot with a path from one hand to another hand it can be found in which case the amplitudes in pulse frequency spectra are higher at different feelings or thoughts.

\* \* \* \* \*